United States Patent
Mishima et al.

(10) Patent No.: US 10,481,138 B2
(45) Date of Patent: *Nov. 19, 2019

(54) CHROMATOGRAM DATA PROCESSING DEVICE AND PROCESSING METHOD

(71) Applicant: SHIMADZU CORPORATION, Kyoto-shi, Kyoto (JP)

(72) Inventors: Kenichi Mishima, Kameoka (JP); Etsuho Kamata, Kameoka (JP); Hiroshi Miura, Kyoto (JP); Yasuhiro Mito, Kyotanabe (JP); Toshinobu Yanagisawa, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 83 days.

This patent is subject to a terminal disclaimer.

(21) Appl. No.: 14/772,432

(22) PCT Filed: Feb. 12, 2014

(86) PCT No.: PCT/JP2014/053165
§ 371 (c)(1),
(2) Date: Sep. 3, 2015

(87) PCT Pub. No.: WO2014/136539
PCT Pub. Date: Sep. 12, 2014

(65) Prior Publication Data
US 2016/0033457 A1    Feb. 4, 2016

(30) Foreign Application Priority Data

Mar. 4, 2013 (JP) ................................ 2013-042107

(51) Int. Cl.
*G01N 30/74* (2006.01)
*G01N 30/86* (2006.01)

(52) U.S. Cl.
CPC ............. *G01N 30/74* (2013.01); *G01N 30/86* (2013.01); *G01N 30/8624* (2013.01); *G01N 30/8675* (2013.01)

(58) Field of Classification Search
CPC .... G01N 30/74; G01N 30/86; G01N 30/8624; G01N 30/8675
(Continued)

(56) References Cited

U.S. PATENT DOCUMENTS

| 6,201,606 B1 * | 3/2001 | Ashibe ...................... G01J 3/28 356/39 |
| 2001/0032923 A1 * | 10/2001 | Koashi .................... G01J 3/433 250/226 |

(Continued)

FOREIGN PATENT DOCUMENTS

| CN | 103765207 A | 4/2014 |
| JP | 2-120662 A | 5/1990 |

(Continued)

OTHER PUBLICATIONS

Communication dated Feb. 26, 2016, from the State Intellectual Property Office of People's Republic of China in counterpart application No. 201480012236.5.

(Continued)

*Primary Examiner* — Mohammed Shamsuzzaman
(74) *Attorney, Agent, or Firm* — Sughrue Mion, PLLC

(57) ABSTRACT

Regarding a chromatogram data processing device configured to process three-dimensional chromatogram data collected on a target sample in which dimensions are made up of time, wavelength, and absorbance, and the chromatogram data processing device includes a differential spectrum generating means configured to generate a differential spectrum that represents a change in a wavelength differential coefficient, which is a differential coefficient in a wavelength (Continued)

direction in a predetermined wavelength range, based on the three-dimensional chromatogram data, with respect to an absorbance spectrum representing a relation of the wavelength and the absorbance at each time in an entire temporal range or a predetermined temporal range, and a determination means configured to determine whether or not one or plural other components are included in a peak of a target component, based on a temporal change in a waveform of the differential spectrum, so that the determination on whether or not a target sample includes impurities can be performed with high accuracy without the requirement of complicated computation processing.

4 Claims, 10 Drawing Sheets

(58) Field of Classification Search
USPC ............................................. 702/25; 73/61.56
See application file for complete search history.

(56) References Cited

U.S. PATENT DOCUMENTS

| | | | | |
|---|---|---|---|---|
| 2004/0194690 | A1* | 10/2004 | Twitchen | C30B 25/105 117/68 |
| 2008/0086038 | A1* | 4/2008 | Thornton | A61B 5/14532 600/310 |
| 2008/0255769 | A1* | 10/2008 | Zhou | G01N 21/3504 702/24 |
| 2009/0232706 | A1 | 9/2009 | Dadala et al. | |
| 2014/0257712 | A1* | 9/2014 | Mito | G01N 30/74 702/25 |
| 2015/0346101 | A1* | 12/2015 | Zhao | G01N 21/47 356/301 |
| 2015/0381953 | A1* | 12/2015 | Egawa | H04N 9/3144 353/31 |
| 2016/0018370 | A1* | 1/2016 | Mito | G01N 30/8631 73/61.56 |
| 2016/0209380 | A1* | 7/2016 | Mishima | G01N 30/8624 |
| 2016/0231297 | A1* | 8/2016 | Noda | G01N 30/74 |
| 2016/0313241 | A1* | 10/2016 | Ochi | G01N 33/02 |

FOREIGN PATENT DOCUMENTS

| | | |
|---|---|---|
| JP | 2936700 B2 | 8/1999 |
| JP | 2011-153966 A | 8/2011 |

OTHER PUBLICATIONS

Grant et al. "Application of derivative spectroscopy to the determination of chromatographic peak purity" Journal of Chromatography, 1985, vol. 347, pp. 219-235 (17 pages total).
Written Opinion for PCT/JP2014/053165 dated Apr. 8, 2014. [PCT/ISA/237].
Yasuhiro Mito, et al., "Shimadzu HPLC—You Foto Daioodo Arei UV-VIS Kenshutsuki SPD-M6A (Shimadzu HPLC Photodiode Array UV-VIS Detector SPD-M6A)", Shimadzu Hyouron (Shimadzu Review), Jul. 1989, pp. 21-28, vol. 46, No. 1.
International Search Report of PCT/JP2014/053165, dated Apr. 8, 2014. [PCT/ISA/210].
Communication dated Feb. 27, 2018, from Intellectual Property of India in counterpart application No. 5892/CHENP/2015.

* cited by examiner

DIFFERENTIAL CHROMATOGRAM OF λx

DIFFERENTIAL CHROMATOGRAM OF λy

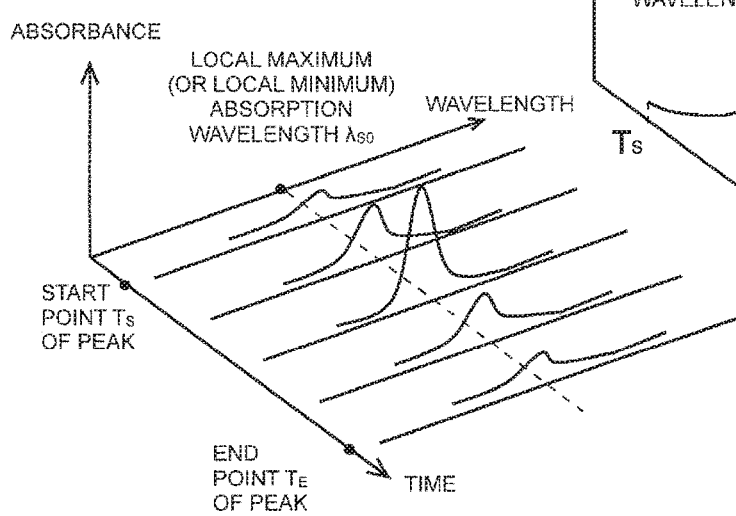
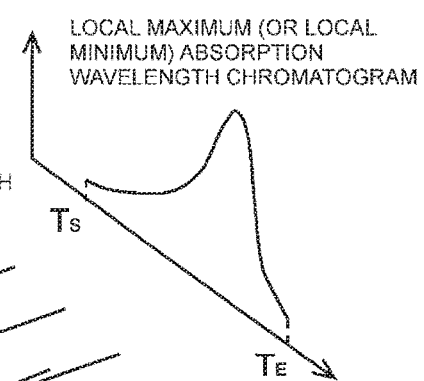
Fig. 15A Prior Art
Fig. 15B Prior Art

CHROMATOGRAM DATA PROCESSING DEVICE AND PROCESSING METHOD

CROSS REFERENCE TO RELATED APPLICATIONS

This application is a National Stage of International Application No. PCT/JP2014/053165 filed Feb. 12, 2014, claiming priority on Japanese Patent Application No. 2013-042107, filed Mar. 4, 2013, the contents of all of which are incorporated herein by reference in their entirety.

TECHNICAL FIELD

The present invention relates to a chromatogram data processing device and a processing method for processing data collected by spectroscopically analyzing samples, in particular, a sample inclusive of components separated by a column of a liquid chromatograph (LC) or a sample introduced by a flow injection method.

BACKGROUND ART

Regarding a liquid chromatograph (LC) in which a multichannel-type detector such as a photo diode array (PDA) detector is used as a detector, an injection time of a sample to a mobile phase is provided as a starting point, and an absorbance spectrum is repeatedly obtained with respect to an eluate from a column, thereby acquiring three-dimensional chromatogram data having three dimensions of time, wavelength, and absorbance. FIGS. 15A and 15B represent the schematic views of the aforementioned three-dimensional chromatogram data. Data on a specific wavelength is extracted from the three-dimensional chromatogram data, thereby generating a wavelength chromatogram indicating a relation of time and absorbance in terms of the specific wavelength. Also, data at a specific time is extracted from the aforementioned three-dimensional chromatogram data, thereby generating an absorbance spectrum indicating a relation of wavelength and absorbance at the specific time.

It is noted that when quantitative analysis of a sole component included in a sample is performed, a flow injection analysis (FIA), in which a column is not used (that is, component separation is not performed), may be used. The FIA method is a method in which a predetermined amount of a sample is injected into a mobile phase being supplied at a constant flow rate by use of an injector for liquid chromatograph, and the sample is introduced to a detector along with the flow of the mobile phase. As is the same with column eluate in a case where the column is used, the concentration of a target component changes in an approximately inverted V-shape with a lapse of time. Data obtained in the case where the sample introduced by the aforementioned FIA method is detected by the multichannel-type detector is also three-dimensional data having three dimensions of time, wavelength, and absorbance, and practically the same with data collected by the liquid chromatograph described above. Accordingly, "three-dimensional chromatogram data" in the present specification includes the three-dimensional data collected by the FIA method.

Regarding the aforementioned liquid chromatograph, when the quantitative analysis on a known target component is performed, generally, a wavelength chromatogram at an absorption wavelength in accordance with the target component is obtained, and a quantitative value is calculated by collating a calibration curve with an area (or height) of a peak originating from the target component that is emerged on the chromatogram.

When the target component is quantitated, there is no problem when the peak emerged on the wavelength chromatogram originates from only the target component. However, a peak is not always based on a sole component (target component), but in some cases, unexpected impurities are included. Accordingly, peak purity determination processing, in which it is examined whether the peak emerged on the chromatogram originates from only the target component or includes impurities, has been performed.

For example, Patent Literature 1 discloses a peak purity determination processing technique for chromatograms obtained by the liquid chromatograph for which the multichannel-type detector is used. In this technique, an absorbance spectrum at a time $T_0$ in accordance with the peak apex of a target peak on the wavelength chromatogram is represented as $S_0(\lambda)$, and an absorbance spectrum at an arbitrary time T prior to or subsequent to the time $T_0$ is represented as $S(\lambda)$, and a coincidence degree P between $S_0(\lambda)$ and $S(\lambda)$ is calculated by the following formula (1):

$$P = \frac{\sum S_0(\lambda) \cdot S(\lambda)}{\sqrt{\sum S_0^2(\lambda) \cdot \sum S^2(\lambda)}} \quad (1)$$

Then, as is illustrated in FIGS. 16A and 16B, the target peak is displayed in such a manner as to be divided along the temporal axis by color in accordance with the coincidence degree P with respect to the peak apex (expressed by shading in the diagram), e.g., in green when the coincidence degree P is from 1.0 to 0.8, or in yellow when the coincidence degree P is from 0.8 to 0.6, or in orange when the coincidence degree P is equal to or less than 0.6.

When the target peak originates from only the target component, as illustrated in FIG. 16A, the coincidence degree P increases in the vicinity of the peak apex and decreases as it moves away from the peak apex, and its shape is approximately symmetrical with respect to the central axis of the peak. In contrast, when another peak exists prior to or subsequent to the peak apex of the target peak (that is, when the target peak includes impurities), the coincidence degree P decreases prior to or subsequent to the peak apex of the target peak. In the example illustrated in FIG. 16B, for example, the coincidence degree P on the right side (on the delayed side in the temporal order) interposing the peak apex is low, compared with the coincidence degree P on the left side. Accordingly, it can be determined that there is a high possibility that impurities are included in the vicinity of the temporal range.

However, regarding the aforementioned conventional peak purity determination method, when the peak of impurities exists in close proximity to the peak apex of the target peak, the coincidence degree P hardly decreases in the proximity of the peak apex, so that there has been a case where the existence of the impurities cannot properly be detected.

Also, regarding the aforementioned peak purity determination method, as disclosed in Non-Patent Literature 1, it is necessary to set a noise vector, for example, whose components are magnitude of noise at each wavelength, as a parameter, in obtaining the threshold of the coincidence degree P for determining whether an impurity peak is included. The problem here is that, in order to obtain the noise vector, the magnitude of noise in a predetermined wavelength area detected by the multichannel-type detector should be successively monitored, and complicated computations of standard deviation in temporal change of the noise in the predetermined wavelength area is required.

CITATION LIST

Patent Literature

Patent Literature 1: JP-B 2936700

Non-Patent Literature

Non-Patent Literature 1: Yasuhiro Mito and Mitsuo Kitaoka, "Shimadzu HPLC-You Foto Daioodo Arei UV-VIS Kenshutsuki SPD-M6A (Shimadzu HPLC Photodiode Array UV-VIS Detector SPD-M6A)", *Shimadzu Hyouron (Shimadzu Review)*, Vol. 46, No. 1 (July 1989), pp. 21-28

SUMMARY OF INVENTION

Technical Problem

The present invention has been achieved to solve the above-mentioned problems. It is an object of the present invention to provide a chromatogram data processing device and a processing method, which can determine whether a target sample includes impurities with high accuracy without requiring complicated computation processing.

Solution to Problem

The present invention, which has been made to achieve the aforementioned object, provides a chromatogram data processing device configured to process three-dimensional chromatogram data collected on a target sample in which dimensions are made up of time, wavelength, and absorbance, and the chromatogram data processing device includes:

a differential spectrum generating means configured to generate a differential spectrum that represents a change in a wavelength differential coefficient, which is a differential coefficient in a wavelength direction in a predetermined wavelength range, based on the three-dimensional chromatogram data, with respect to the absorbance spectrum representing a relation of the wavelength and the absorbance at each time in an entire temporal range or a predetermined temporal range; and a determination means configured to determine whether or not one or plural other components are included in a peak of a target component, based on a temporal change in a waveform of the differential spectrum.

It is desirable that the determination means be configured to find a wavelength at which a differential coefficient regarding the differential spectrum at each time reaches zero, and configured to determine whether or not one or plural other components are included in the peak of the target component based on a temporal change in the wavelength.

It is desirable that the chromatogram data processing device according to the present invention further include a display means configured to display the temporal change in the wavelength at which the differential coefficient regarding the differential spectrum at each time reaches zero.

Typically, the aforementioned three-dimensional chromatogram data is obtained by repeatedly acquiring the absorbance spectrum with respect to the sample that includes the component separated in the temporal direction by the column of the chromatograph, by means of detectors such as the multichannel-type detector.

Also, in place of the sample through the column, similar data obtained with respect to the sample introduced without separating the components by the FIA method may be applied.

Also the aforementioned detector is not necessarily of the multichannel-type detector, and any detector may be used as long as a spectrum, whose waveform can be differentiated, can be obtained. Accordingly, an ultraviolet and visible spectrophotometer, an infrared spectrophotometer, a near-infrared spectrophotometer, a fluorescence spectrophotometer and the like, which obtain the absorbance spectrum by wavelength scanning, may be used.

Also, the aforementioned chromatograph may be any of the liquid chromatograph and the gas chromatograph.

The absorbance spectrum represents the relation of the wavelength of light from the sample and the absorbance of each wavelength. In the absorbance spectrum, a local maximum (and a local minimum in some cases) absorption wavelength that is unique to each material exists. In many cases, a plurality of local maximum (or local minimum) absorption wavelengths exist for each material, but when the absorbance spectrum is limited in a range of predetermined wavelengths, only one local maximum (or local minimum) absorption wavelength may emerge.

A local maximum (or local minimum) absorption wavelength is unique to materials, and the local maximum (or local minimum) absorption wavelengths of different components normally do not coincides with each other. Even when one local maximum (or local minimum) absorption wavelength of a component incidentally coincides with a local maximum (or local minimum) absorption wavelength of another component, still another local maximum (or local minimum) absorption wavelengths which are different from each other may exist. Thus, when other component is not included in the peak (target peak) originating from the target component on the chromatogram, the maximum (or minimum) absorption wavelength of the target component remains at its maximum (or minimum) regarding the absorbance spectrum at each time point in a range of time during which at least the target peak is included. For this reason, the waveform of differential spectrums representing the change in the differential coefficient in the wavelength direction of the absorbance spectrum are analogous, and the wavelength (which is the local maximum (or local minimum) absorption wavelength) at which the differential coefficient reaches zero is constant at all times and does not change.

In contrast, when another component is included in the target peak on the chromatogram, the local maximum (or local minimum) absorption wavelength changes, and the wavelength at which the differential coefficient in the wavelength direction of the absorbance spectrum reaches zero changes. Even when the peak of another component exists in close proximity of the apex of the target peak (that is, even when the retention times are close), the local maximum (or local minimum) absorption wavelength slightly changes, so that the chromatogram data processing device according to the present invention can determine with high accuracy whether or not another component (impurity) is included in the target sample.

Also, with the aforementioned construction, it is only necessary to obtain the absorbance spectrum at each time, but it is not required to reconfigure the chromatogram for a wavelength except for wavelengths set at the time of real-time display based on the data obtained by accumulating the absorbance spectrum repeatedly obtained and detect the peak in the chromatogram, so that the presence or absence of an impurity or impurities can be determined in real time, and the time required for the determination can be reduced.

Advantageous Effects of the Invention

According to the chromatogram data processing device and the processing method according to the present invention, even when the peak of an impurity exists in close proximity of the apex of target peak on the chromatogram, which the conventional peak purity determination fails to detect, whether or not an impurity is included in the target peak can be determined with high accuracy. Also, as is different from the aforementioned conventional peak purity determination processing, it is not necessary to set the noise vector as a parameter, so that whether or not an impurity is included in the target peak can be determined with relatively simple computation processing. Furthermore, the presence or absence of an impurity or impurities can be determined in real time, the time required for the determination can be reduced. The entire temporal changes in the wavelengths (which is the local maximum (or local minimum) absorption wavelength) at which the differential coefficient in the wavelength direction of the absorbance spectrum reaches zero are examined in the entire range of wavelengths at which the absorbance spectrum is obtained, so that the determination results can be obtained with high accuracy.

BRIEF DESCRIPTION OF DRAWINGS

FIG. 15A is a schematic view illustrating three-dimensional chromatogram data and 15B is a schematic views illustrating the local maximum (or local minimum) absorption wavelength chromatogram generated based on the three-dimensional chromatogram data.

FIG. 16A represents the example of a peak in which impurities are not included, and FIG. 16B represents a peak in which impurities are included.

DESCRIPTION OF EMBODIMENTS

[Constitution and Operation of Chromatogram Data Processing Device of First Embodiment of Present Invention]

Figure 1:
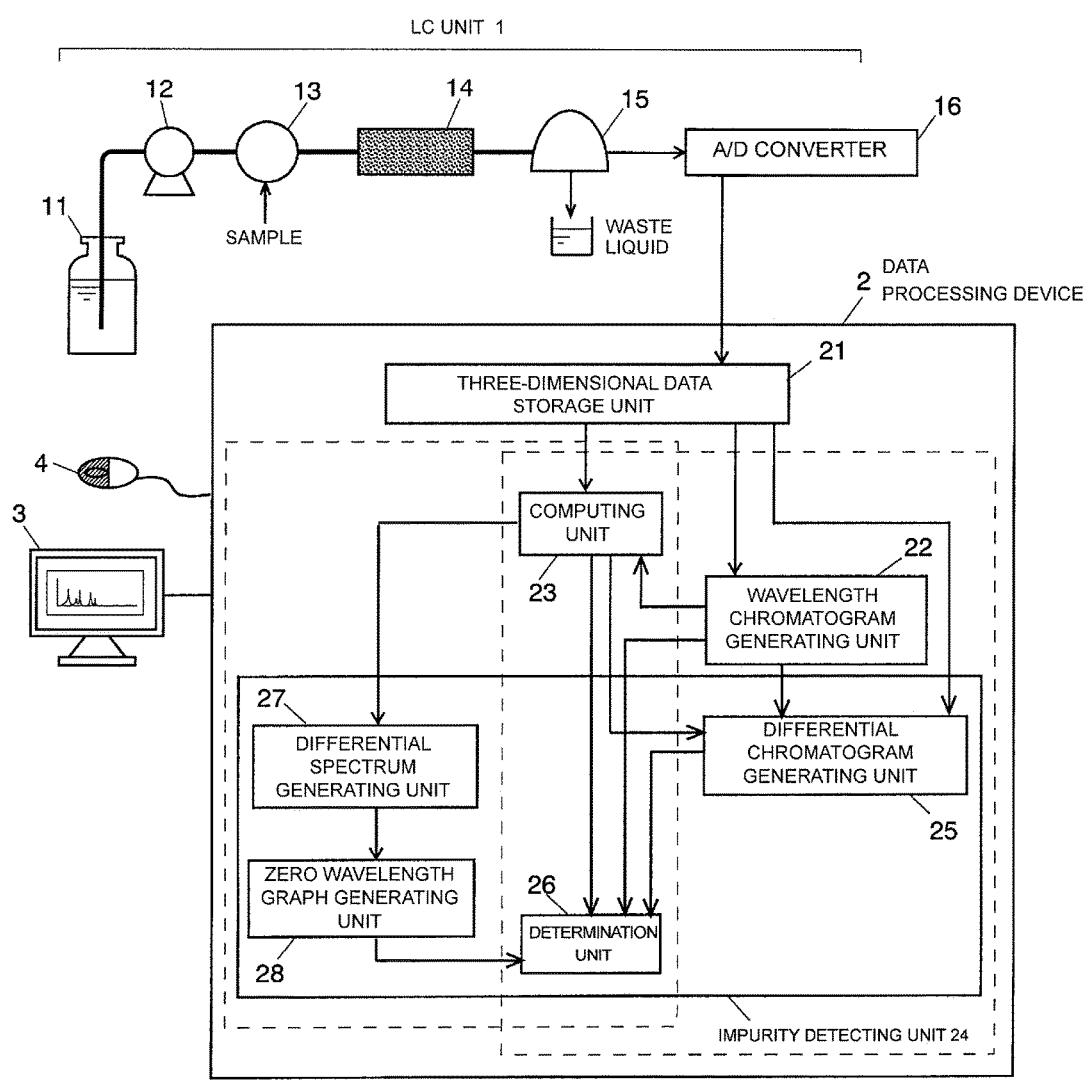
FIG. 1 is a schematic configuration view of a liquid chromatograph system that includes a chromatogram data processing device of the present invention.

First, a first embodiment of a chromatogram data processing device according to the present invention will be described referring to FIG. 1. FIG. 1 is a schematic configuration view of a liquid chromatograph system that includes the chromatogram data processing device (hereinafter, merely referred to as "data processing device") of the present embodiment.

In an LC unit 1 that collects three-dimensional chromatogram data, a liquid delivery pump 12 draws a mobile phase from a mobile phase container 11 and supplies the mobile phase to a sample injection unit 13 at a constant flow rate. The sample injection unit 13 injects a sample into the mobile phase at a predetermined timing. The sample is delivered by the mobile phase to a column 14, and respective components in the sample are separated in the temporal direction while the sample passes through the column 14, and sample components are eluted from the column 14.

A PDA detector 15, which is a sort of multichannel-type detector, is provided at the exit of the column 14, as a detector for detecting the sample components in an eluate from the column 14. The PDA detector 15 emits light from a light source not illustrated to the eluate, and disperses the wavelengths of the light passing through the eluate and approximately simultaneously detects the intensity of the light of each wavelength by means of a PDA linear sensor. A detected signal obtained by the PDA detector 15 is converted into a digital signal by means of an A/D converter 16, and is subsequently outputted to a data processing device 2.

The data processing device 2 includes a three-dimensional data storage unit 21 that stores the detection signal of each wavelength outputted from the A/D converter 16 at a time t as three-dimensional chromatogram data, a wavelength chromatogram generating unit 22, a computing unit 23, and an impurity detecting unit 24 that detects impurities.

The impurity detecting unit 24 includes a differential chromatogram generating unit 25, a determination unit 26, a differential spectrum generating unit 27, and a zero wavelength graph generating unit 28, as functional blocks. The operations of these units are described later.

A display unit 3 displays various pieces of information such as a local maximum (or local minimum) absorption wavelength chromatogram, an absorbance spectrum, a differential chromatogram, a differential spectrum, determination results, and the like. An operating unit 4 is operated by an operator in order to input and set necessary information for data processing, such as a data acquisition time $t_{end}$ and the local maximum (or local minimum) absorption wavelength $\lambda_0$ of a target component.

It is noted that part or whole of functions of the data processing device 2 can be achieved by executing dedicated control and processing software installed in a personal computer or a workstation. Also, the display unit 3 is a general liquid crystal monitor or the like, and the operating unit 4 can be a pointing device such as a keyboard or a mouse, which is a standard instrument equipped with the personal computer or the workstation.

Next, the principle of peak purity determination in the present embodiment will be described. In the present embodiment, a method of determining peak purity based on the temporal change of the wavelength differential coefficient of a specific wavelength obtained by differentiating the absorbance spectrum with respect to the wavelength (differential chromatogram), and a method of determining the peak purity based on the temporal change in a wavelength at which the wavelength differential coefficient of the absorbance spectrum in a range of predetermined wavelengths reaches zero are selectively executed. Hereinafter, the principles of the aforementioned purity determinations will be described in order.

[Two-Component Peak Separation and Peak Purity Determination Based on Differential Chromatogram]

Figure 3:
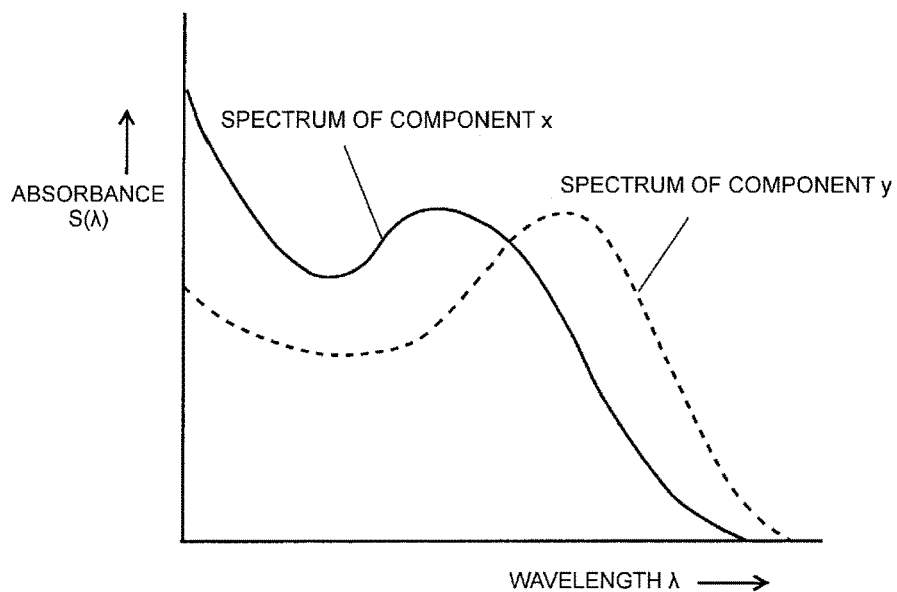
FIG. 3 is a view illustrating one example of an absorbance spectrum to explain the principles of two-component separation and peak purity determination of the present invention.

Now, it is assumed that three-dimensional chromatogram data illustrated in FIGS. 15A and 15B includes two components of x and y, each of which is included in a sample. FIG. 3 is a view illustrating one example of respective absorbance spectra of a component x (target component x) and a component y (other component y). As is illustrated, generally, the local maximum (or local minimum) absorption wavelength corresponding to the apex (local maximum (or local minimum) point) of the absorbance peak differs depending on materials.

Figure 4:
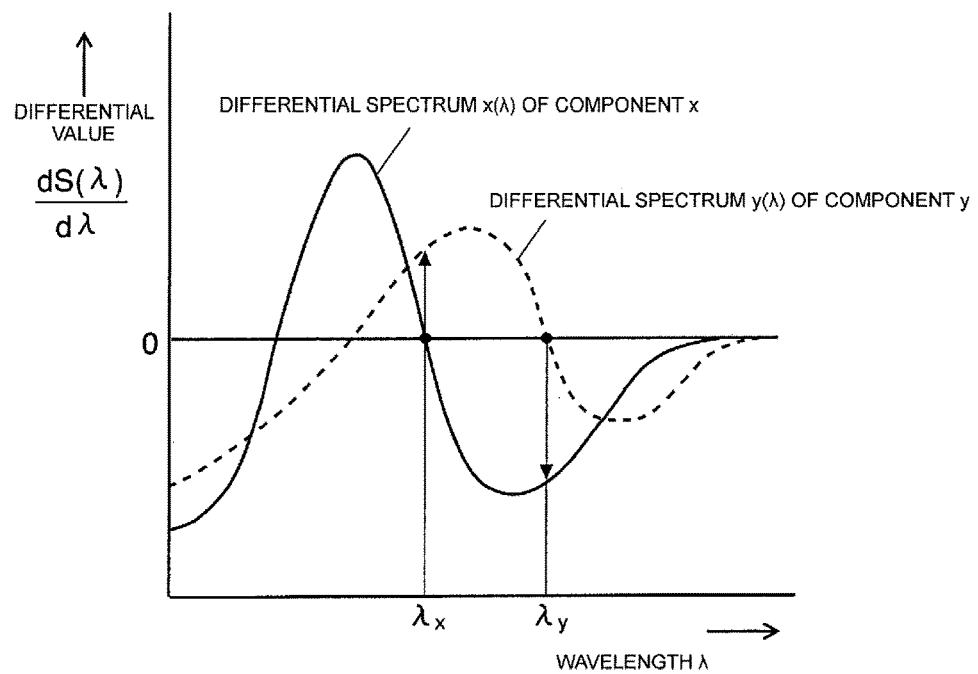
FIG. 4 is view illustrating a differential spectrum based on the absorbance spectrum illustrated in FIG. 3.

FIG. 4 represents a differential spectrum obtained by differentiating the absorbance spectrum illustrated in FIG. 3 with respect to the wavelength. A differential coefficient is a positive value in a phase in which a curve ascends in the wavelength direction, and the differential coefficient is a negative value in a phase in which the curve descends, and the differential coefficient reaches zero at the apex of the absorbance peak and on the bottom of a trough. As illustrated in FIG. 4, a wavelength at which the differential coefficient with respect to the differential spectrum of the component x reaches zero (the differential coefficient reaches "zero" in a situation where the differential coefficient changes from a positive value to a negative value) is represented as $\lambda_x$, and a wavelength at which the differential coefficient with respect to the differential spectrum of the component y reaches zero (similarly, the differential coefficient reaches "zero" in a situation where the differential coefficient changes from a positive value to a negative value) is represented as $\lambda_y$. That is, herein, $\lambda_x$ is the local maximum absorption wavelength of the component x, and $\lambda_y$ is the local maximum absorption wavelength of the component y.

Figure 5:
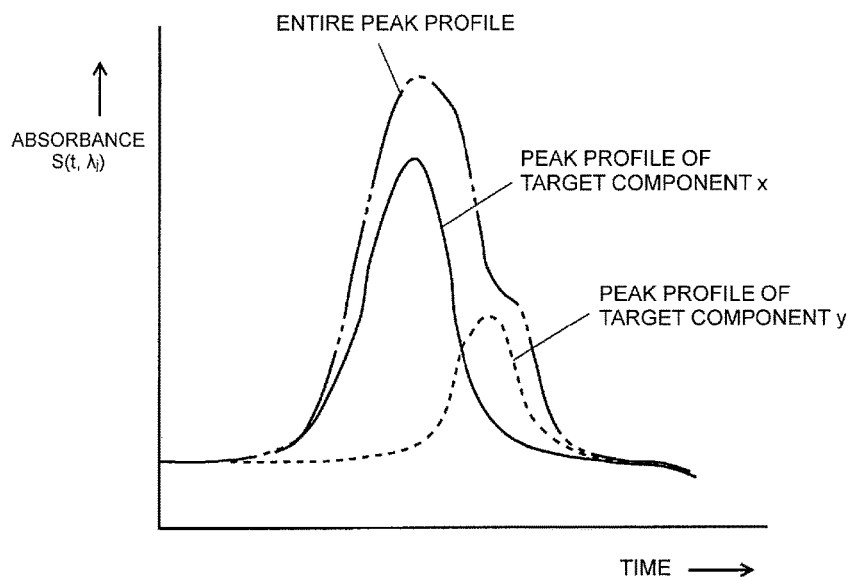
FIG. 5 is a view illustrating two-component mixed peaks on the chromatogram.

FIG. 5 is a view illustrating one example of respective peak profiles of the component x and the component y on the chromatogram, and the peak profile in a state where the peaks are overlapped, that is, unseparated mixed peak. The retention times of the component x and the component y are considerably analogous, so that it is difficult to predict the peak profiles of the component x and the component y based on the mixed peaks.

Accordingly, the following method is used.

Here, when it is assumed that the absorbance spectrum of the component x is represented as $x(\lambda)$, and the peak profile of the component x is represented as $a(t)$, and similarly, the absorbance spectrum of the component y is represented as $y(\lambda)$, and the peak profile of the component y is represented as $b(t)$, a three-dimensional chromatogram $S(t, \lambda)$ in two-component system in which the component x and the component y both are eluted (that is, the peaks are overlapped on the chromatogram) can be represented by the following formula (2).

$$S(t,\lambda)=a(t)x(\lambda)+b(t)y(\lambda) \qquad (2)$$

When $S(t, \lambda)$ is partially differentiated by a wavelength $\lambda$, a formula (3) is provided as follows:

$$\partial S(t,\lambda)/\partial \lambda = a(t)x'(\lambda)+b(t)y'(\lambda) \qquad (3)$$

The wavelength $\lambda x$, for which the differential coefficient of the differential spectrum of the component x reaches 0, is substituted in the formula (3), and $x'(\lambda x)=0$ leads to a formula (4) as follows:

$$\partial S(t,\lambda x)/\partial \lambda = b(t)y'(\lambda x) \qquad (4)$$

Similarly, the wavelength $\lambda y$, for which the differential coefficient of the differential spectrum of the component y reaches 0, is substituted in the formula (3), and $y'(\lambda y)=0$ leads to a formula n (5) as follows:

$$\partial S(t,\lambda y)/\partial \lambda = a(t)x'(\lambda y) \qquad (5)$$

Figure 6A:
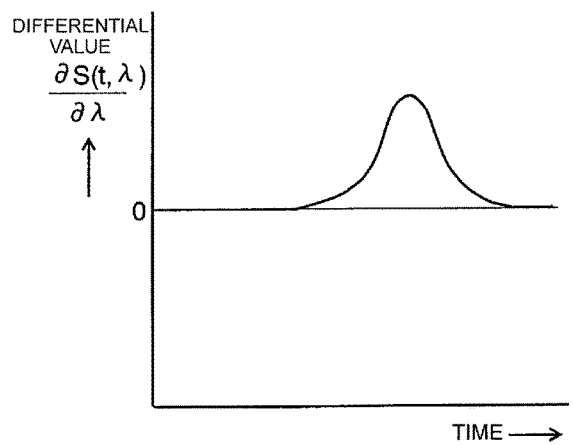
FIGS. 6A and 6B are views illustrating differential chromatograms based on the differential spectrum illustrated in FIG. 4.
Figure 6B:
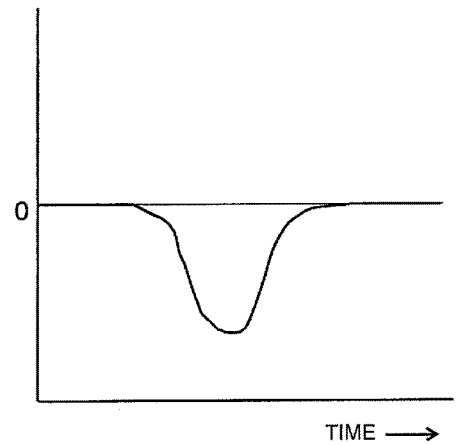

FIG. 6A is a graph representing the plotted results of the formula (4) in the temporal direction, and similarly, FIG. 6B is a graph representing the plotted results of the formula (5) in the temporal direction. That is, FIG. 6A is a differential chromatogram at the wavelength $\lambda x$, and FIG. 6B is a differential chromatogram at the wavelength $\lambda y$. As is obvious in the formula (4), the peak profile b(t) only based on the component y emerges on the differential chromatogram at the wavelength $\lambda x$. Also, as is obvious in the formula (5), the peak profile a(t) only based on the component x emerges on the differential chromatogram at the wavelength $\lambda y$. The areas or heights of the peak profiles a(t) and b(t) depend on the concentration of respective components. It is noted that the aforementioned description regarding FIG. 4, FIGS. 5, 6A and 6B is applied in a case where the local maximum absorption wavelengths $\lambda x$ and $\lambda y$ of the components x and y are used, but the local minimum absorption wavelengths of the components x and y may be used in place of the local maximum absorption wavelengths.

Now, an attention is paid to FIG. 6A, and when no peak emerges on the differential chromatogram, that is, when a differential coefficient remains zero, this means that no component y exists. That is, the presence or absence of the overlap of the component y can be determined by determining whether or not the peak appears on the differential chromatogram at the local maximum (or local minimum) absorption wavelength $\lambda x$ of the component x. If only this determination is performed, it is not required that the local maximum (or local minimum) absorption wavelength $\lambda y$ of the component y is known, and it is obvious that the component y itself may be an unknown component. This concept is extended. If it is merely determined whether or not the peak of the chromatogram of a certain known component includes other component, it is understood that such other component may be plural, and one component to a plurality of components may be collectively treated as impurities.

That is, the three-dimensional chromatogram of the component x is $a(t)x(\lambda)$, and when another one component to a plurality of another components is/are mixed into the peak as impurities, the three-dimensional chromatogram S(t, λ) can be represented by the following formula (6):

$$S(t,\lambda)=a(t)x(\lambda)+b(t)y(\lambda)+c(t)z(\lambda)+\ldots \quad (6)$$

When the three-dimensional chromatogram S(t, λ) is partially differentiated by a wavelength λ, and a wavelength λx at which the value of the differential spectrum x'(λ) of the component x reaches zero is substituted in the formula (6), the following formula (7) is represented as:

$$\partial S(t,\lambda x)/\partial \lambda = b(t)y'(\lambda x)+c(t)z'(\lambda x)+\ldots \quad (7)$$

The formula (7) is the differential chromatogram at the local maximum (or local minimum) absorption wavelength λx of the component x, and the peak originating from the component x is removed, and it is found that only the peak of impurities emerges.

Accordingly, it is understood that the presence or absence of impurities mixed in the target component (component x) can be determined based on the same principle of the aforementioned two-component peak separation.

Thus, according to the aforementioned determination method, the presence or absence of an impurity or impurities is determined based on the temporal change on the differential chromatogram at one local maximum (or local minimum) absorption wavelength λx of the target component (component x).

[Peak Purity Determination Based on Differential Spectrum]

Figure 7:
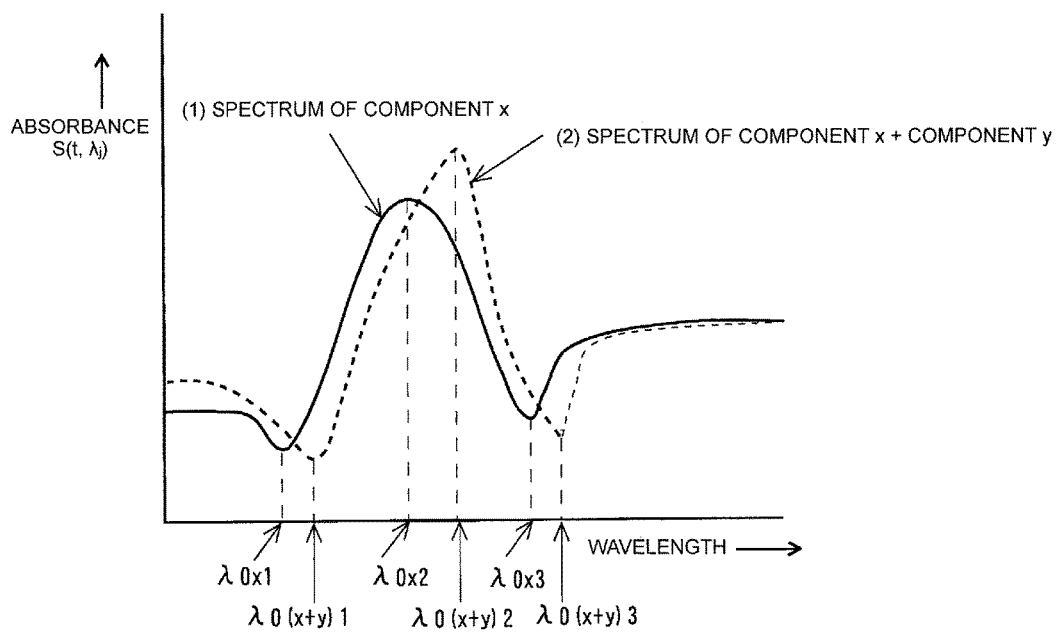
FIG. 7 is a view illustrating the absorbance spectrum of the component x and the absorbance spectrum of the mixture of the component x and the component y.

As described above, the local maximum (or local minimum) absorption wavelength in accordance with the apex (local maximum (or local minimum) point) of the absorbance peak of the absorbance spectrum S(t, λ) differs depending on materials, and the local maximum (or local minimum) absorption wavelength is unique to each material. Thus, the local maximum (or local minimum) absorption wavelengths of different components normally do not correspond to each other (see FIG. 3). Accordingly, when two components (component x and component y) are included in the target sample, as illustrated in FIG. 7, the apex of the absorbance peak fluctuates. The same is applied to a case where three components or more are included in the target sample. Accordingly, whether the two components or more are included in the target sample, that is, whether impurities are included can be determined by observing the temporal change in the wavelength corresponding to the apexes of the absorbance peaks of the absorbance spectrums S(t, λ).

Figure 8:
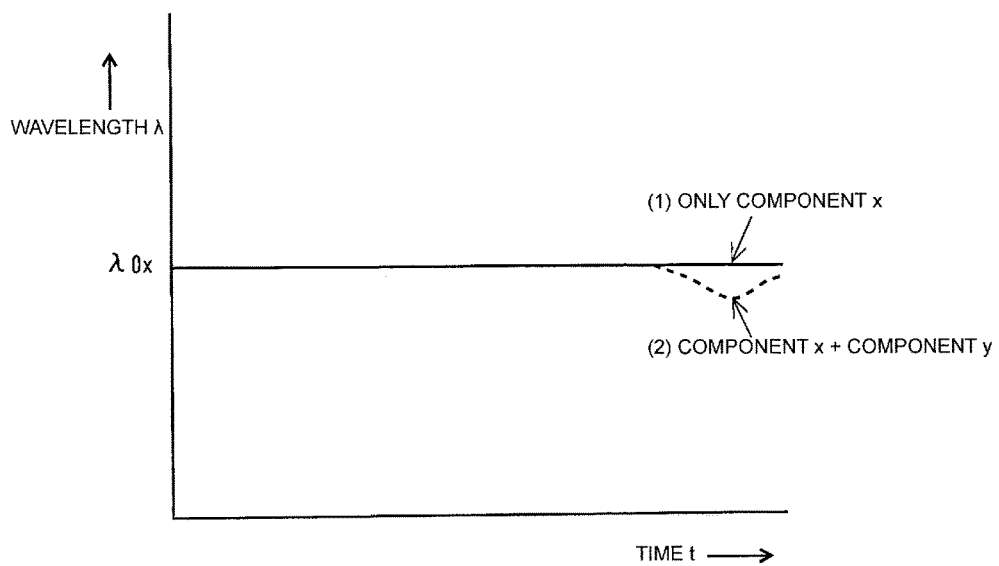
FIG. 8 is a view illustrating a wavelength $\lambda_{0x}$ at which the differential coefficient $S'(t, \lambda)$ at a time t with respect to the component x (solid line) and the mixture of the component x and the component y (dashed line) reaches zero.

That is, when other component is not included in the peak originating from the target component (component x) on the chromatogram, the local maximum (or local minimum) absorption wavelength of the target component remains at its local maximum (or local minimum) regarding the absorbance spectrum at each time point in a range of time during which at least the peak originating from the target component is included. For this reason, the wavelength (which is the local maximum (or local minimum) absorption wavelength) at which the differential coefficient in the wavelength direction of the absorbance spectrum at each time reaches zero is constant at all times and does not change ((1) in FIG. 8).

In contrast, when other component (component y) is included in the peak originating from the target component (component x), the local maximum (or local minimum) absorption wavelength of the target component (component x) changes under the influence of other component (component y) regarding the absorbance spectrum at each time point in a range of time during which other component (component y) is included ((2) in FIG. 7). For this reason, the wavelength (which is the local maximum (or local minimum) absorption wavelength) at which the differential coefficient in the wavelength direction of the absorbance spectrum at a time t reaches zero changes in the range of time ((2) in FIG. 8).

Accordingly, it is understood that the presence or absence of impurities (component y) mixed in the target component (component x) can be determined based on the temporal change (FIG. 8) in the wavelength corresponding to the apexes of the absorbance peaks of the absorbance spectrums S(t, λ), that is, the wavelength at which the differential coefficient obtained by differentiating the absorbance spectrum with respect to the wavelength at each time reaches zero.

Regarding the second determination method, even when the local maximum (or local minimum) absorption wavelength is unknown, the presence or absence of impurities can be determined based on only the absorbance spectrum obtained at each time, which makes it possible to easily determine the presence or absence of impurities in real time. Here, "real time" means that every time the absorbance spectrum is obtained without waiting the completion of chromatograph analysis, the presence or absence of impurities is determined.

When the local maximum (or local minimum) absorption wavelength is limited in a range of predetermined wavelengths, only one local maximum (or local minimum) absorption wavelength may emerge in some cases. However, as described above, in many cases, the local maximum (or local minimum) absorption wavelength is unique to each material in which a plurality of local maximum (or local minimum) absorption wavelengths exist. Therefore, the local maximum (or local minimum) absorption wavelengths of different components normally do not correspond to each other, and even when one local maximum (or local minimum) absorption wavelength, out of the plurality of local maximum (or local minimum) absorption wavelengths, incidentally corresponds to another local maximum (or local minimum) absorption wavelength, still another local maximum (or local minimum) absorption wavelengths which are different from each other exist. Accordingly, the determination method based on the aforementioned differential chromatogram is employed, there is a possibility in which it is determined that impurities are not included due to a wavelength differential coefficient of a certain one local maximum (or local minimum) absorption wavelength coincidentally matched. However, based on the determination method herein, a plurality of wavelengths at which the differential coefficient in the wavelength direction of the absorbance spectrum at each time reaches zero in the entire wavelength areas can be examined ($\lambda_{0\times 1}$, $\lambda_{0\times 2}$, and $\lambda_{0\times 3}$ in FIG. 7), so that the inclusion of impurities can be determined with high accuracy.

Figure 2:
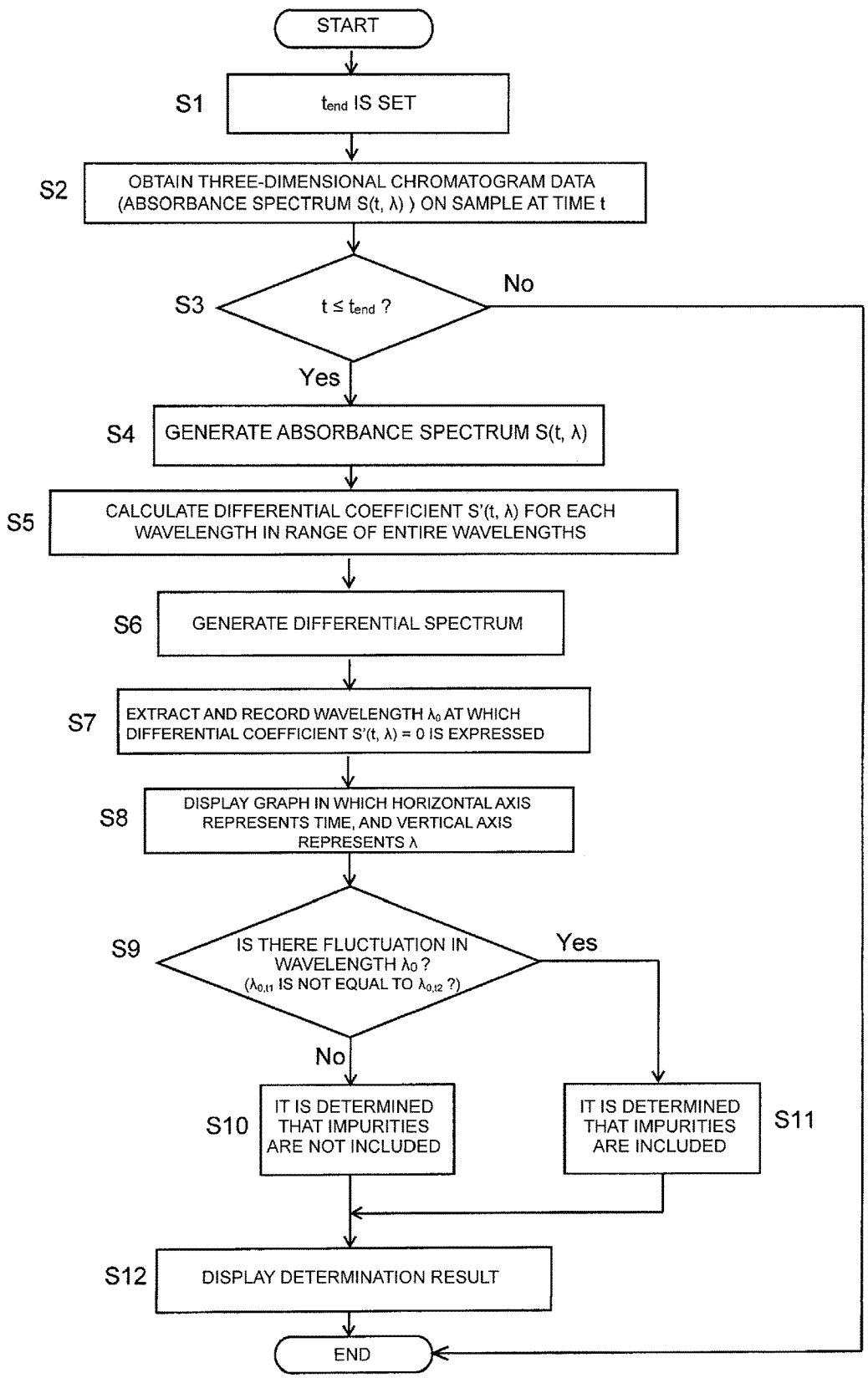
FIG. 2 is a flowchart illustrating the operation of processing of determination on the presence or absence of an impurity or impurities in the chromatogram data processing device of the first embodiment of the present invention.

Next, the data processing operation of the peak purity determination in the liquid chromatograph system of the present embodiment will be described. First, the data processing operation of the determination method based on the differential spectrum will be described referring to the flowchart in FIG. 2.

An operator sets a finish time $t_{end}$ of the data acquisition by means of the operating unit 4 after the start of the chromatograph analysis (Step S1). It is noted that, herein, the description will be given where the data immediately after the start of the chromatograph analysis is acquired, but the start time and finish time of the data acquisition may be set.

When the chromatograph analysis is carried out for the target sample in the LC unit 1, the absorbance (detection signal) of each wavelength at a time t in a range of predetermined wavelengths is outputted from the PDA detector 15 to the three-dimensional data storage unit 21 and stored in the three-dimensional data storage unit 21 (Step S2).

First, the computing unit 23 determines whether or not the time t exceeds the time $t_{end}$ (Step S3). When it is determined that the time t does not exceed the time $t_{end}$, the computing unit 23 generates the absorbance spectrum S(t, λ) which represents the relation of absorbance and wavelength at the time t stored in the three-dimensional data storage unit 21 (Step S4), differentiates the absorbance spectrum in the range of the entire wavelengths in the wavelength direction, thereby calculating a differential coefficient S'(t, λ) (Step S5) for every wavelength. When it is determined that the time t exceeds the time $t_{end}$, the determination is finished.

Subsequently, the differential spectrum generating unit 27 generates a differential spectrum that represents the relation of the wavelength and the differential coefficient S'(t, λ) calculated by the computing unit 23 (Step S6). After that, the zero wavelength graph generating unit 28 extracts a wavelength $λ_0$ at which the differential coefficient reaches zero from the differential spectrum and records the wavelength $λ_0$ (Step S7). Finally, a graph in which the horizontal axis represents time, and the vertical axis represents the wavelength $λ_0$ is displayed on the display unit 3 (Step S8).

Steps S2 to S8 are carried out without waiting for the completion of chromatograph analysis every time the absorbance spectrum is obtained, and resultant points are plotted on the graph, in which the horizontal axis represents time, and the vertical axis represents the wavelength $λ_0$, on the display unit 3 in real time. Accordingly, the operator can determine in real time whether or not two components or more are included in the target sample, that is, whether or not impurities are included, based on the shape of the graph plotted.

Also, in the present embodiment, when the value of the wavelength $λ_{0,t1}$ at which the differential coefficient S'(t, λ) is zero at a time $t_1$ is compared with the value of the wavelength $λ_{0,t2}$ at which the differential coefficient S'(t, λ) is zero at a time t2 immediately before the time $t_1$ (Step S9), and a difference between the values is within a predetermined range (that is, No in Step S9 in FIG. 2), the determination unit 26 determines that impurities are not included in the target sample up to the time t, that is, the target sample consists of only one component (Step S10). In contrast, when the difference between the value of the wavelength $λ_{0,t1}$ at which the differential coefficient S'(t, λ) is zero at the time $t_1$ and the value of the wavelength $λ_{0,t2}$ at which the differential coefficient S'(t, λ) is zero at a time $t_2$ immediately before the time $t_1$ exceeds the predetermined range (that is, Yes in Step S9 in FIG. 2), the determination unit 26 determines that the target sample includes impurities (Step S11). The determination results thus obtained are informed to the operator via the display unit 3 (Step S12).

As is the same with the case of single wavelength $λ_0$, when there are a plurality of values of the wavelength $λ_0$ at which the differential coefficient S'(t, λ) is zero at the time t (for example, $λ_{0×1}$, $λ_{0×2}$, and $λ_{0×3}$ regarding (1) component x in FIG. 7), the aforementioned Steps S9 to S12 are performed for each wavelength $λ_0$ ($λ_{0×1}$, $λ_{0×2}$, and $λ_{0×3}$), and the presence or absence of impurities is determined, so that the determination can be performed with further accuracy.

As described above, in the present embodiment, even when impurities are included in close vicinity of the peak apex of the target component, the local maximum (or local minimum) absorption wavelength $λ_0$ at which the differential coefficient S'(t, λ) obtained by differentiating the absorbance spectrum S(t, λ) with respect to the wavelength reaches zero changes due to the inclusion of the impurities. Accordingly, the determination results with markedly high accuracy can be obtained, compared with the conventional peak purity determination method. Also, the local maximum (or local minimum) absorption wavelengths in the range of the entire wavelengths of the absorbance spectrums obtained at each time are examined, so that the accuracy of the determination results is enhanced, compared with a case where the chromatogram of the single local maximum (or local minimum) absorption wavelength of the target component is estimated. Furthermore, the determination can be made in real time, so that it is possible to reduce the time required for the determination.

Regarding the data processing device 2 according to the present embodiment, as is different from the aforementioned conventional technique, it is not necessary to set a noise vector made up of the noise component at each wavelength as a parameter, so that the peak purity determination can be performed with markedly simple computation processing, compared with the conventional technique.

It is noted that the finish time $t_{end}$ of the data acquisition after the start of the chromatograph analysis is initially set in the aforementioned description, but it may be such that the finish time $t_{end}$ is not specifically set in a case where the data acquisition is performed over the entire time of measurements, and the aforementioned Steps S2 to S12 are performed with respect to the entire absorbance spectra obtained.

Also, the display of the temporal change in the wavelength $λ_0$ displayed on the display unit 3 in Step S6 is not specifically limited to the aforementioned graph, but, for example, a table may be displayed as long as the display is easily recognized.

Next, the data processing operation of the peak purity determination based on the differential chromatogram will be described referring to FIGS. 9 to 14.

First, when the chromatograph analysis with respect to the target sample is carried out in the LC unit 1, the absorbance (detection signal) of each wavelength at a time t in a range of predetermined wavelengths is outputted from the PDA detector 15 to the three-dimensional data storage unit 21 and stored in the three-dimensional data storage unit 21 (Step S1).

Subsequently, the operator inputs the wavelength value of the local maximum (or local minimum) absorption wavelength $λ_{S0}$ of the target component (for example, the component required to be quantitated) included in the sample by means of the operating unit 4 (Step S2). Upon receiving the input value, the wavelength chromatogram generating unit 22 generates the local maximum (or local minimum) absorption wavelength chromatogram in which each point of intersection of the horizontal axis representing time and the vertical axis representing absorbance at the local maximum (or local minimum) absorption wavelength $λ_{S0}$ is plotted, based on the local maximum (or local minimum) absorption wavelength $λ_{S0}$ input, and the absorbance data stored in the three-dimensional data storage unit 21 (Step S3). FIG. 15B illustrates one example of the local maximum (or local minimum) absorption wavelength chromatogram generated based on the three-dimensional chromatogram data illustrated in FIG. 15A.

Figure 10:
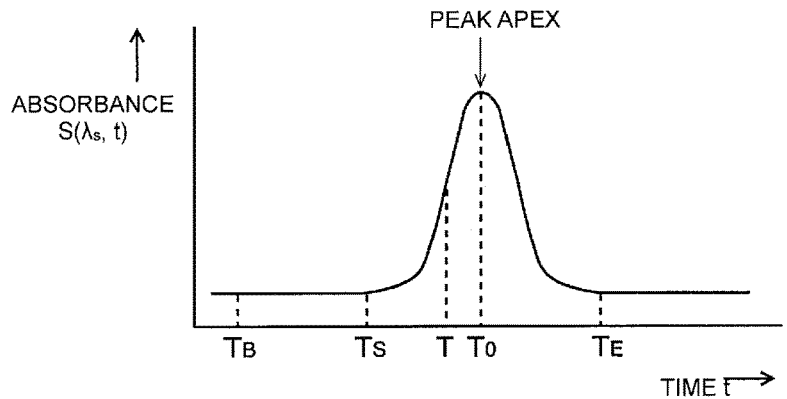
FIG. 10 is a view illustrating one example of the peak of a maximum (or minimum) absorption wavelength chromatogram.

The computing unit 23 sequentially examines the inclination of the curve of the local maximum (or local minimum) absorption wavelength chromatogram generated by the wavelength chromatogram generating unit 22 in the temporal direction, as illustrated in FIG. 10, determines a start point $T_S$ of a peak at the time when the inclination amount of the curve reaches a predetermined value or higher, a peak apex $T_0$ at the time when the inclination amount of the curve changes from a positive value to zero and further into a negative value, and a finish point $T_E$ of a peak in at the time when the absolute value of the inclination amount of the curve reaches a predetermined value or lower, and detects the peak (Step S4). FIG. 10 illustrates only one peak, but when the plurality of components are included in the sample, a plurality of peaks are normally detected. Information on the peak detected is displayed on the display unit 3, and the operator selects a target peak originating from the target component from among the plurality of peaks by means of the operating unit 4 (Step S5).

Figure 13:
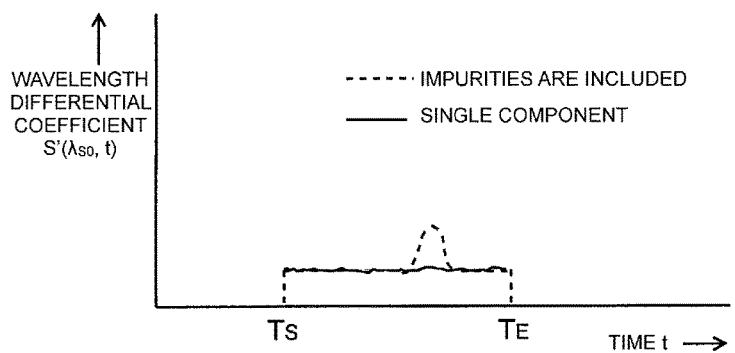
FIG. 13 is a view illustrating one example of a differential chromatogram.

When the target peak is selected, the differential chromatogram generating unit 25 acquires the absorbance spectrum in a temporal range from the start point $T_S$ to the finish point $T_E$ of the target peak from the three-dimensional data storage unit 21 and calculates the wavelength differential coefficient of the absorbance at the maximum (or minimum) absorption wavelength $\lambda_{S0}$ of the target component, which is set by use of the operating unit 4 with respect to each absorbance spectrum (Step S6). Then, the differential chromatogram, in which each point of intersection of the horizontal axis representing time and the vertical axis representing the wavelength differential coefficient calculated is plotted, is generated (Step S7). FIG. 13 illustrates one example of the differential chromatogram.

The determination unit 26 determines the presence or absence of impurities in the temporal range from the start point $T_S$ to the finish point $T_E$ of the target peak by carrying out the following processing based on the aforementioned principle, based on the differential chromatogram generated by the differential chromatogram generating unit 25.

Figure 12:
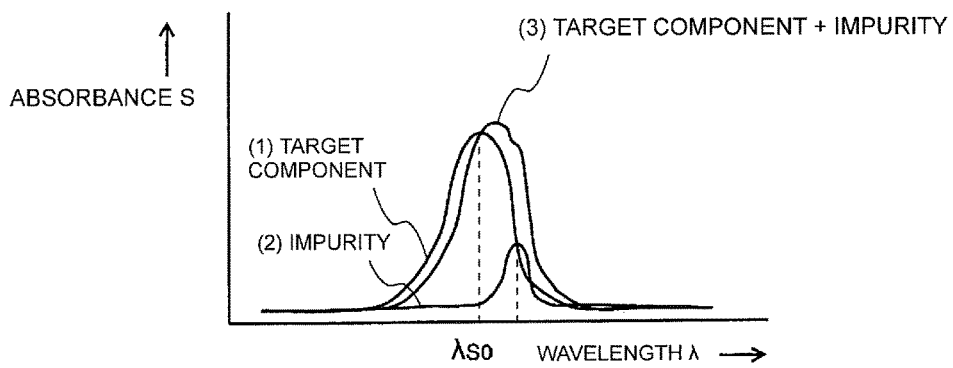
FIG. 12 is a view illustrating one example of the absorbance spectra of a target component and impurities.

FIG. 12 is a view schematically illustrating the pattern ((1) in FIG. 12) of the absorbance spectrum of the target component and the pattern ((2) in FIG. 12) of the absorbance spectrum of an impurity at a certain time $T_U$ during the chromatograph analysis. Thus, when the absorption wavelength range of the target component and the absorption wavelength range of the impurity are overlapped with each other, the pattern of the absorbance spectrum actually obtained at the time $T_U$ is represented by adding the pattern of the absorbance spectrum of the target component and the pattern of the absorbance spectrum of the impurity ((3) in FIG. 12). Accordingly, the local maximum (or local minimum) position of the absorbance spectrum does not coincident with the local maximum (or local minimum) absorption wavelength $\lambda_{S0}$ of the target component.

Figure 11:
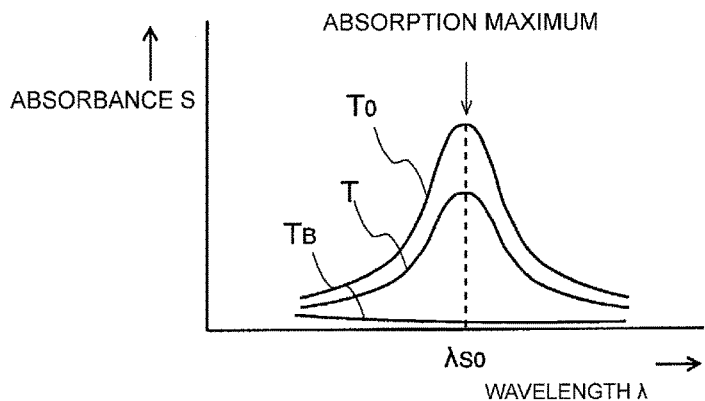
FIG. 11 is a view illustrating one example of the absorbance spectra at each measuring time.

When the target peak originates from only the target component, as illustrated in FIG. 11, at any time point between the start point $T_S$ and the finish point $T_E$ of the target peak, the local maximum (or local minimum) absorption wavelength $\lambda_{S0}$ of the target component coincident with the local maximum (or local minimum) position of the absorbance spectrum at each time, so that the wavelength differential coefficient at the local maximum (or local minimum) absorption wavelength $\lambda_{S0}$ reaches zero. Accordingly, the differential chromatogram in the temporal range from the start point $T_S$ to the finish point $T_E$ of the target peak depicts a flat state though only inevitable noise is included, as illustrated by a solid line in FIG. 13. In contrast, when the target peak includes an impurity, as illustrated in FIG. 12, the local maximum (or local minimum) absorption wavelength $\lambda_{S0}$ of the target component fails to coincide with the local maximum (or local minimum) position of the absorbance spectrum at each time, as a result, the wavelength differential coefficient at the local maximum (or local minimum) absorption wavelength $\lambda_{S0}$ has values except for zero in the temporal range from the start point $T_S$ to the finish point $T_E$. Accordingly, the differential chromatogram is not in a flat state in the temporal range during which an impurity is included, as illustrated by a dotted line in FIG. 13.

Consequently, the determination unit 26 determines whether or not the differential chromatogram is flat in the temporal range from the start point $T_S$ to the finish point $T_E$ of the target peak (Step S8). When the differential chromatogram is flat in the temporal range (Yes in Step S8 in FIG. 9), the determination unit 26 determines that the target peak does not include an impurity in the temporal range, that is, that the peak originates from only the target component (Step S9). In contrast, when the differential chromatogram is not flat in the temporal range (that is, No in Step S8), the determination unit 26 determines that the target peak includes the impurity in the temporal range (Step S10). The determination results thus obtained are informed to the operator via the display unit 3 (Step S11).

The determination on whether or not the differential chromatogram is flat, for example, may be performed based on the determination on whether or not there exists a peak that is N times higher than the average noise intensity of the baseline or that is equal to or higher than a predetermined peak area. Alternatively, other determination methods may be applied.

Thus, regarding the determination method, when the local maximum (or local minimum) absorption wavelength slightly deviates from the local maximum (or local minimum) absorption wavelength $\lambda_{S0}$ of the target component, the presence or absence of the impurity is reflected in the shape of the differential chromatogram. Accordingly, the determination results with markedly high accuracy can be obtained, compared with the conventional peak purity determination method.

Also, as is different from the aforementioned conventional technique, it is not necessary to set the noise vector made up of the noise component at each wavelength as a parameter, so that the peak purity determination can be performed with markedly simple computation processing, compared with conventional technique.

Furthermore, in the present embodiment, the differential chromatogram is generated by narrowing down the temporal range from the start point $T_S$ to the finish point $T_E$ of the target peak, not over the entire range of measuring time, so that it can be more efficiently determined whether or not the impurity is included in the target peak, and the determination can be completed in a shorter period of time.

Figure 9:
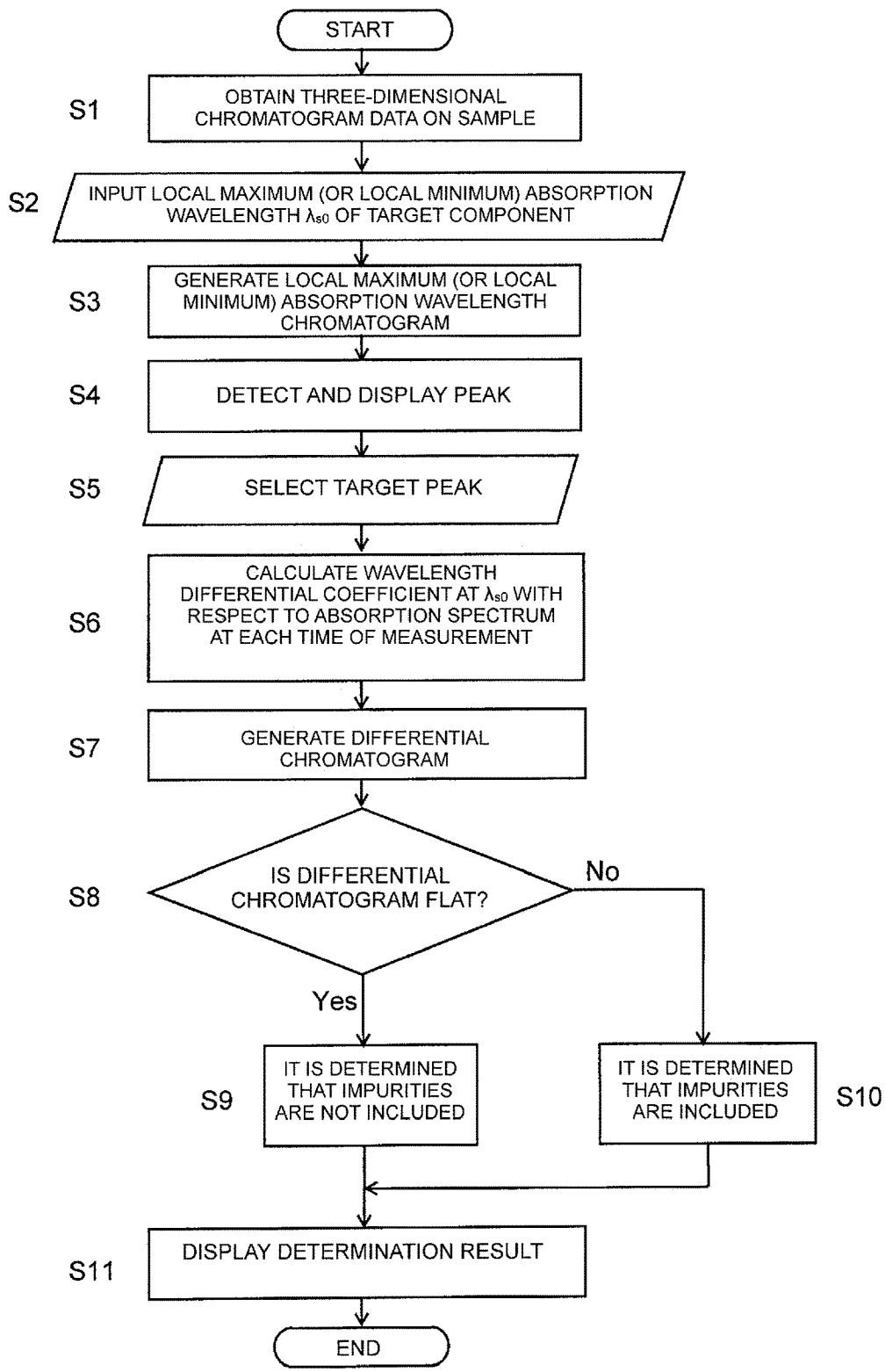
FIG. 9 is a flowchart illustrating the operation of peak purity determination processing of the chromatogram data processing device of another embodiment of the present invention.

It is noted that the operator selects the target peak by means of the operating unit 4 in the aforementioned description, but in this time, the operator may select a plurality of peaks, not sole peak, as the target peak. In this case, the detection of impurities as described above may be carried out for every target peak selected. Also, it may be set in advance in such a manner that the detection of impurities is carried out for the entire peaks detected, irrespective of the number of peaks detected. In this case, the detection of impurities is automatically carried out for the entire peaks, and thus the processing in Step S5 in the flowchart of FIG. 9 is omitted.

Also, in the present embodiment, in Step S2, the operator inputs the wavelength value of the local maximum (or local minimum) absorption wavelength $\lambda_{S0}$ of the target component. However, when the detection of impurities is carried out based on the differential chromatogram, unless the wavelength value of the local maximum (or local minimum) absorption wavelength $\lambda_{S0}$ of the target component, that is, the wavelength value at which the differential coefficient S'(t, λ) reaches zero is accurately set, the peak of the target component cannot be removed in differentiating the absorbance spectrum in the wavelength direction. Specifically, it is necessary to set the wavelength at which the differential coefficient S'(t, λ) reaches zero with a precision of the order of 0.01 nm, but it is practically difficult for the operator to set the wavelength value at which the differential coefficient S'(t, λ) reaches zero with such precision. Also, even when the operator can designate the wavelength from the absorbance spectrum displayed on the display unit 3, the setting of the wavelength requires the precision of the order of 0.01 nm, as a result, it is necessary to set the wavelength after the spectrum displayed is sufficiently enlarged, which takes a trouble of setting the wavelength.

Accordingly, it may be such that the operator designates an approximate position of the wavelength at which S'(t, λ) reaches zero on the screen on which the absorbance spectrum is displayed, and an accurate wavelength at which S'(t, λ) reaches zero in the vicinity of the approximate wavelength is automatically detected.

Figure 14:
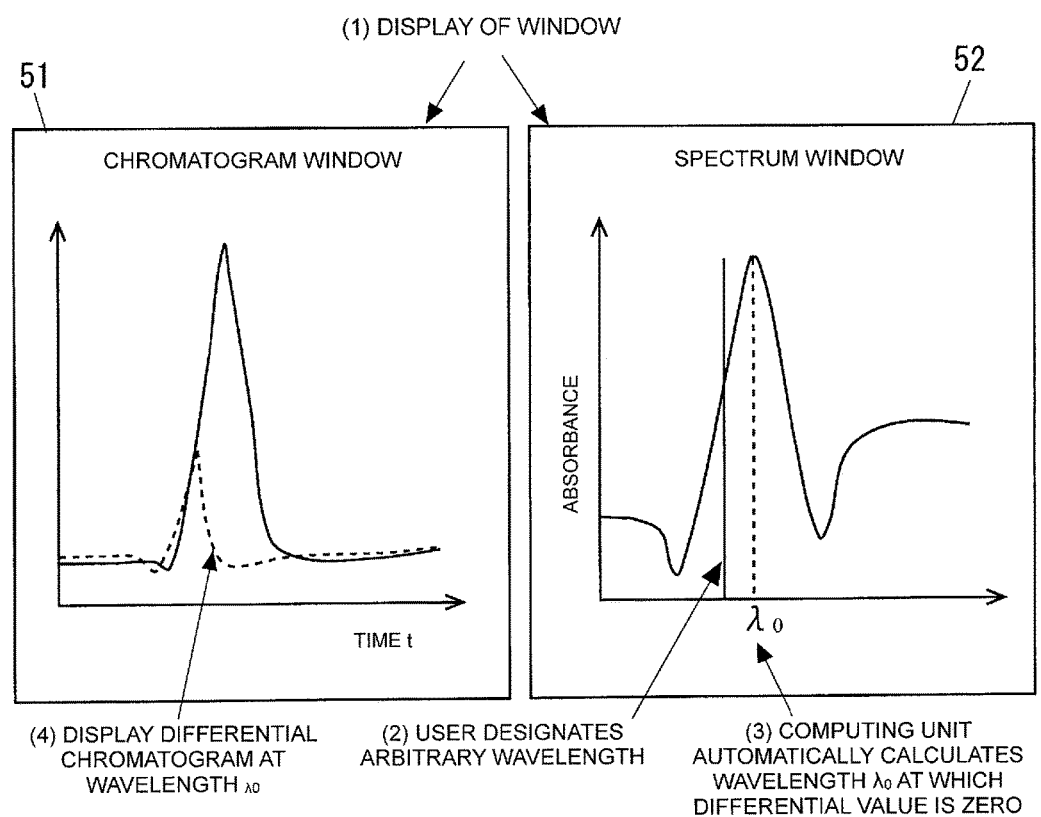
FIG. 14 is a view illustrating a chromatogram window and a spectrum window.
Figure 16A:
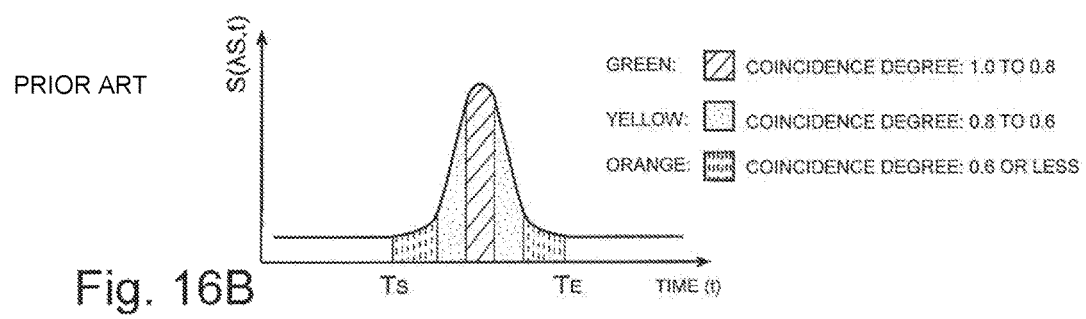
FIGS. 16A and 16B are display examples of results obtained by the conventional technique of peak purity determination processing.
Figure 16B:
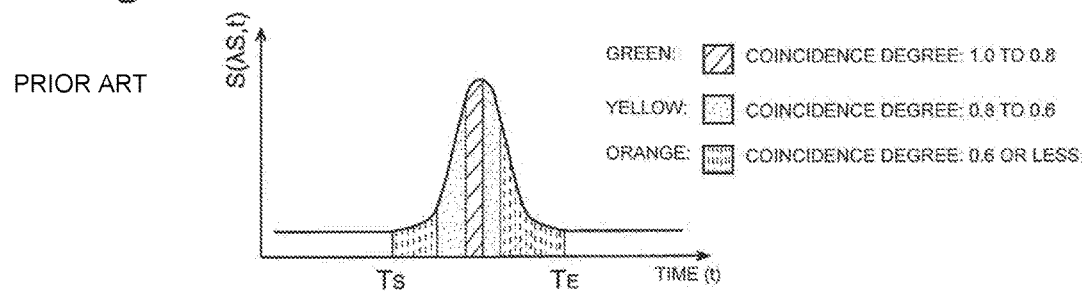

Specifically, a chromatogram window 51 and a spectrum window 52 are displayed on the display unit 3 as a user interface ((1) in FIG. 14). First, the operator designates a wavelength close to the local maximum value or the local minimum value (the wavelength at which the differential coefficient S'(t, λ) reaches zero) of the absorbance spectrum on the spectrum window 52 with a cursor ((2) in FIG. 14). Then, the computing unit 23 calculates the wavelength $\lambda_0$ at which the differential value is zero which is closest to the wavelength designated by the operator ((3) in FIG. 14). When the wavelength $\lambda_0$ is obtained, the computing unit 23 calculates a differential coefficient of the wavelength $\lambda_0$ as described above and displays the differential chromatogram on the display unit 3 ((4) in FIG. 14).

Thus, the chromatogram window 51 and the spectrum window 52 are prepared on the display unit 3 as a user interface, and the operator can obtain the accurate wavelength $\lambda_0$ at which the differential value is zero by only designating the proximity of the position of the desired wavelength on the absorbance spectrum, and verify the differential chromatogram at the wavelength $\lambda_0$ thus displayed. That is, the necessity for the operator to examine the wavelength in advance at which the differential coefficient obtained by differentiating the absorbance spectrum with respect to the wavelength reaches zero is eliminated or the necessity for the operator to input an accurate wavelength at which the differential coefficient reaches zero on the absorbance spectrum is eliminated, so that the operator can obtain the differential chromatogram of a target wavelength in a more intuitive manner in a shorter period of time.

It is noted that, as the inputting method of the wavelength value of the local maximum (or local minimum) absorption wavelength $\lambda_{S0}$ of the target component, besides the aforementioned method, a wavelength value in accordance with the designation by the operator of a name or a structural formula of a target component may be retrieved from a database. When the target component includes a plurality of local maximum (or local minimum) absorption wavelengths, one of the wavelengths may be used.

Furthermore, regarding the setting for the temporal range in which the target peak is included, it may be such that the operator inputs the temporal range in which appropriate temporal width is set before and after the retention time of the target peak on the wavelength chromatogram, in advance by means of the operating unit 4, thereby obtaining a time $T_S$ corresponding to the start point and a time $T_E$ corresponding to the finish point of the target peak.

Also, it may be such that the wavelength chromatogram as illustrated in FIG. 10 is displayed on the screen of the display unit 3, and the operator recognizes the wavelength chromatogram and designates the time $T_S$ corresponding to the start point and the time $T_E$ corresponding to the finish point of the target peak by means of the operating unit 4.

In the case of the aforementioned constitution, in Step S5, the operator directly inputs the temporal range or designates the positions of the start point and the finish point of the target peak on the wavelength chromatogram by a click operation or the like, so that the temporal range from the start point $T_S$ to the finish point $T_E$ of the target peak can be determined.

Furthermore, when the plurality of local maximum (or local minimum) absorption wavelengths exist, generally, it is preferable that the wavelength having the maximum intensity among them be selected. Also, regarding the local maximum (or local minimum) absorption wavelength $\lambda_{S0}$ of the target component, when existence of the impurity peak in the vicinity of the peak apex of the target peak and the amount of the impurity needs to be determined, the local maximum (or local minimum) absorption wavelength at which a value obtained by differentiating the absorbance spectrum of the impurity with respect to the wavelength is sufficiently large may be selected.

It is obvious that any of modification, addition, and correction added to the present invention within the gist of the present invention is within the scope of claims of the present application.

For example, the chromatograph detector that acquires the three-dimensional chromatogram data which is the target processed by the data processing device of the present invention is not required to be the multichannel-type detector such as a PDA detector, any detector may be applied as long as a spectrum whose waveform can be differentiated can be obtained, in such a manner that when the absorbance of the absorbance spectrum is sequentially differentiated with respect to the wavelength, the differential coefficient accurately reflected based on the inclination of the spectral curve can be obtained. However, it is not appropriate to take too much time for the measurement of the absorbance over a range of predetermined wavelengths. Accordingly, an ultraviolet and visible spectrophotometer, an infrared spectrophotometer, a near-infrared spectrophotometer, a fluorescence spectrophotometer or other spectrophotometers, which can perform high-speed wavelength scanning, may be employed.

Also, not the liquid chromatograph, but a gas chromatograph may be employed as the chromatograph but the chromatograph for which the aforementioned detector is used is normally the liquid chromatograph. Also, as described above, it is obvious that the present invention can be applied to devices or methods of processing not only the data obtained by detecting the sample separated through the column of the chromatograph by means of the detector, but also the data obtained by detecting the components by means of the detector in the sample introduced without separating the components by the FIA method.

REFERENCE SIGNS LIST

1 . . . LC Unit
11 . . . Mobile Phase Container
12 . . . Liquid Delivery Pump
13 . . . Sample Injection Unit
14 . . . Column
15 . . . PDA Detector
16 . . . A/D Converter
2 . . . Data Processing Device
21 . . . Three-Dimensional Data Storage Unit
22 . . . Wavelength Chromatogram Generating Unit
23 . . . Computing Unit
24 . . . Impurity Detecting Unit
25 . . . Differential Chromatogram Generating Unit
26 . . . Determination Unit
27 . . . Differential Spectrum Generating Unit
28 . . . Zero Wavelength Graph Generating Unit
3 . . . Display Unit
4 . . . Operating Unit
51 . . . Chromatogram Window
52 . . . Spectrum Window

The invention claimed is:

1. A system, comprising:
a chromatograph including a column that separates components of a target sample and a detector that detects the separated components;
a chromatogram data processing device configured to process three-dimensional chromatogram data collected on the detected separated components of the target sample in which dimensions are made up of time, wavelength, and absorbance, and generate an absorbance spectrum representing a relation of the wavelength and the absorbance;
a display configured to display a window of the absorbance spectrum;
an operating unit configured to receive a wavelength designated on the absorbance spectrum displayed by an operator,
wherein the chromatogram data processing device is configured to act as:
a computing unit configured to calculate a specific wavelength closest to the wavelength designated by the operator, the specific wavelength being either one of a local maximum absorption wavelength and a local minimum absorption wavelength of the target sample at which a differential coefficient reaches zero on the absorbance spectrum;
a differential chromatogram generating unit configured to calculate a differential coefficient at the specific wavelength of the absorbance spectrum obtained at each time and configured to generate a differential spectrum at each time that represents a change in the differential coefficient at the specific wavelength; and
a determination unit configured to determine whether or not one or plural other components are included a peak of a target component, based on the change in the differential coefficient at each time, and whether or not the target sample includes impurities.

2. The system according to claim 1,
wherein the determination unit is configured to find a wavelength at which the differential coefficient at each time reaches zero, and configured to determine whether or not one or plural other components are included in the peak of the target component, based on a temporal change in the wavelength.

3. The system according to claim 2, wherein the display is configured to display the temporal change in the wavelength at which the differential coefficient at each time reaches zero.

4. A method, comprising:
separating components of a target sample using a column of a chromatograph and detecting the separated components;
processing, by a data processing device, three-dimensional chromatogram data collected on the detected separated components of the target sample in which dimensions are made up of time, wavelength, and absorbance, and generating an absorbance spectrum representing a relation of the wavelength and the absorbance;
displaying a window of the absorbance spectrum;
receiving a wavelength designated on the absorbance spectrum displayed by an operator,
wherein the processing comprises:
calculating a specific wavelength closest to the wavelength designated by the operator, the specific wavelength being either one of a local maximum absorption wavelength and a local minimum absorption wavelength of the target sample at which a differential coefficient reaches zero on the absorbance spectrum;
calculating a differential coefficient at the specific wavelength of the absorbance spectrum obtained at each time;
generating a differential spectrum at each time that represents a change in the differential coefficient at the specific wavelength; and
determining whether or not one or plural other components are included in a peak of a target component, based on the change in the differential coefficient at each time, and whether or not the target sample includes impurities.

* * * * *